United States Patent
Inoue

(10) Patent No.: US 10,441,148 B2
(45) Date of Patent: Oct. 15, 2019

(54) ILLUMINATION LENS AND ILLUMINATION OPTICAL SYSTEM FOR AN ENDOSCOPE

(71) Applicant: FUJIFILM Corporation, Tokyo (JP)

(72) Inventor: Kazuki Inoue, Saitama (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

(21) Appl. No.: 15/980,145

(22) Filed: May 15, 2018

(65) Prior Publication Data

US 2018/0333047 A1 Nov. 22, 2018

(30) Foreign Application Priority Data

May 19, 2017 (JP) .................. 2017-100266

(51) Int. Cl.
| | |
|---|---|
| *A61B 1/06* | (2006.01) |
| *A61B 1/00* | (2006.01) |
| *G02B 23/24* | (2006.01) |
| *F21V 5/00* | (2018.01) |
| *A61B 1/07* | (2006.01) |

(52) U.S. Cl.
CPC ........ *A61B 1/0623* (2013.01); *A61B 1/00096* (2013.01); *A61B 1/07* (2013.01); *G02B 23/2461* (2013.01); *F21V 5/008* (2013.01)

(58) Field of Classification Search
CPC ... A61B 1/00096; A61B 1/0623; F21V 5/008; G02B 23/2461
USPC ........................................................ 362/331
See application file for complete search history.

(56) References Cited

U.S. PATENT DOCUMENTS

| | | | |
|---|---|---|---|
| 8,118,734 B2 | 2/2012 | Murayama | |
| 8,979,316 B2* | 3/2015 | Lee | F21V 5/002 |
| | | | 362/268 |
| 2005/0174771 A1* | 8/2005 | Conner | G02B 27/0961 |
| | | | 362/244 |
| 2006/0052668 A1* | 3/2006 | Homma | A61B 1/00096 |
| | | | 600/177 |
| 2007/0147041 A1* | 6/2007 | Shiratsuchi | F21V 5/007 |
| | | | 362/268 |
| 2008/0051636 A1* | 2/2008 | Murayama | A61B 1/00096 |
| | | | 600/176 |

FOREIGN PATENT DOCUMENTS

| | | |
|---|---|---|
| JP | 4147037 B2 | 9/2008 |
| JP | 4874032 B2 | 2/2012 |

\* cited by examiner

*Primary Examiner* — William N Harris
(74) *Attorney, Agent, or Firm* — Sughrue Mion, PLLC

(57) ABSTRACT

An illumination lens consists of two lenses consisting of a first lens and a second lens arranged in this order from a light source side, and surfaces of all the lenses have a planar shape or a convexly spherical shape. An incident surface of the first lens is a convex surface, and an emission surface of the second lens is a flat surface. An intersection of a ray incident in parallel to an optical axis at a height of 0.25×H and a ray incident in parallel to the optical axis at a height of 0.5×H is positioned only inside the illumination lens in a case in which an outer diameter of the first lens is denoted by 2H. Predetermined Conditional Expression related to a focal length of the illumination lens and a focal length of the first lens is satisfied.

9 Claims, 2 Drawing Sheets

EXAMPLE 1

EXAMPLE 2

ILLUMINATION LENS AND ILLUMINATION OPTICAL SYSTEM FOR AN ENDOSCOPE

CROSS-REFERENCE TO RELATED APPLICATIONS

The present application claims priority under 35 U.S.C. § 119 to Japanese Patent Application No. 2017-100266, filed on May 19, 2017. The above application is hereby expressly incorporated by reference, in its entirety, into the present application.

BACKGROUND OF THE INVENTION

1. Field of the Invention

The present invention relates to an illumination lens that can be applied to an illumination device of an endoscope or the like, and an illumination optical system for an endoscope that includes the illumination lens.

2. Description of the Related Art

In the past, illumination optical systems disclosed JP4147037B and JP4874032B to be described below have been known as an illumination optical system of an endoscope. Each of JP4147037B and JP4874032B discloses a lens system that consists of two lenses, is combined with a fiber bundle guiding light generated from a light source at the time of use, and irradiates an object with illumination light.

SUMMARY OF THE INVENTION

As the angle of an observation optical system of an endoscope is widen, the angle of an illumination optical system of an endoscope is required to be widened. Since high energy is generated at the convergence point of light in the case of a certain design specification in an optical system that converges light generated from a light source and then emits the converged light as divergent light to obtain wide-angle illumination light, it is necessary to be careful so that light does not invade an object to be observed. Particularly, low-invasive light is desired in a medical endoscope to reduce a patient's burden.

However, a plurality of convergence points of light are formed in a case in which parallel light is incident on a condenser lens consisting of two lenses disclosed in JP4147037B, and one convergence point of the convergence points is positioned close to an object to be observed present outside the condenser lens. Accordingly, the condenser lens needs to be considered in terms of low-invasive light. Further, the position of a convergence point of light in a case in which parallel light is incident on the lens system is not clearly specified in JP4874032B. However, since the position of a convergence point may be changed from a designed value due to a variation caused by manufacturing tolerance even if the convergence point is positioned inside the lens system, the condenser lens needs to be considered in terms of this.

The invention has been made in consideration of the above-mentioned circumstances, and an object of the invention is to provide an illumination lens that has wide-angle light distribution characteristics and can obtain low-invasive illumination light, and an illumination optical system for an endoscope including the illumination lens.

An illumination lens of the invention is an illumination lens that is used in an illumination optical system for an endoscope. The illumination lens consists of two lenses consisting of a first lens and a second lens arranged in this order toward an object side from a light source side. Surfaces of all the lenses have a planar shape or a convexly spherical shape, an incident surface of the first lens on which light generated from a light source is to be incident is a convex surface, and an emission surface of the second lens from which light toward an object is to be emitted is a flat surface. An intersection of a ray incident on the incident surface in parallel to an optical axis at a height of 0.25×H from the optical axis and a ray incident on the incident surface in parallel to the optical axis at a height of 0.5×H from the optical axis is positioned only inside the illumination lens in a case in which an outer diameter of the first lens in a direction perpendicular to the optical axis is denoted by 2H. In a case in which a thickness of the second lens along the optical axis is denoted by t, a position of the intersection in a direction of the optical axis is positioned closer to the light source than a position, which is apart from the emission surface of the second lens to the light source side by 0.4×t. Conditional Expression (1) expressed by "0.61<f/f1<1.5 ... (1)" is satisfied in a case in which a focal length of the illumination lens is denoted by f and a focal length of the first lens is denoted by f1.

In the illumination lens of the invention, it is preferable that the following Conditional Expression (1-1) is satisfied.

$$0.62 < f/f1 < 1.49 \qquad (1\text{-}1)$$

Further, in the illumination lens of the invention, in a case in which a refractive index of the first lens with respect to a d line is denoted by Nd1, it is preferable that the following Conditional Expression (2) is satisfied and it is more preferable that the following Conditional Expression (2-1) is satisfied.

$$1.8 < Nd1 < 2 \qquad (2)$$

$$1.83 < Nd1 < 2 \qquad (2\text{-}1)$$

Furthermore, in the illumination lens of the invention, in a case in which a focal length of the illumination lens is denoted by f and a focal length of the second lens is denoted by f2, it is preferable that the following Conditional Expression (3) is satisfied and it is more preferable that the following Conditional Expression (3-1) is satisfied.

$$0.4 < f/f2 < 1.8 \qquad (3)$$

$$0.45 < f/f2 < 1.75 \qquad (3\text{-}1)$$

Moreover, in the illumination lens of the invention, in a case in which a refractive index of the second lens with respect to a d line is denoted by Nd2, it is preferable that the following Conditional Expression (4) is satisfied and it is more preferable that the following Conditional Expression (4-1) is satisfied.

$$1.8 < Nd2 < 2 \qquad (4)$$

$$1.83 < Nd2 < 2 \qquad (4\text{-}1)$$

An illumination optical system for an endoscope of the invention comprises the illumination lens of the invention.

"Consist of" in this specification may intend to include a lens substantially not having a power; optical elements other than a lens, such as a stop, a filter, and a cover glass; a lens flange; a lens barrel; and the like other than elements serving as components.

According to the invention, it is possible to provide an illumination lens that has wide-angle light distribution characteristics and can obtain low-invasive illumination light, and an illumination optical system for an endoscope including the illumination lens.

DESCRIPTION OF THE PREFERRED EMBODIMENTS

Figure 1:
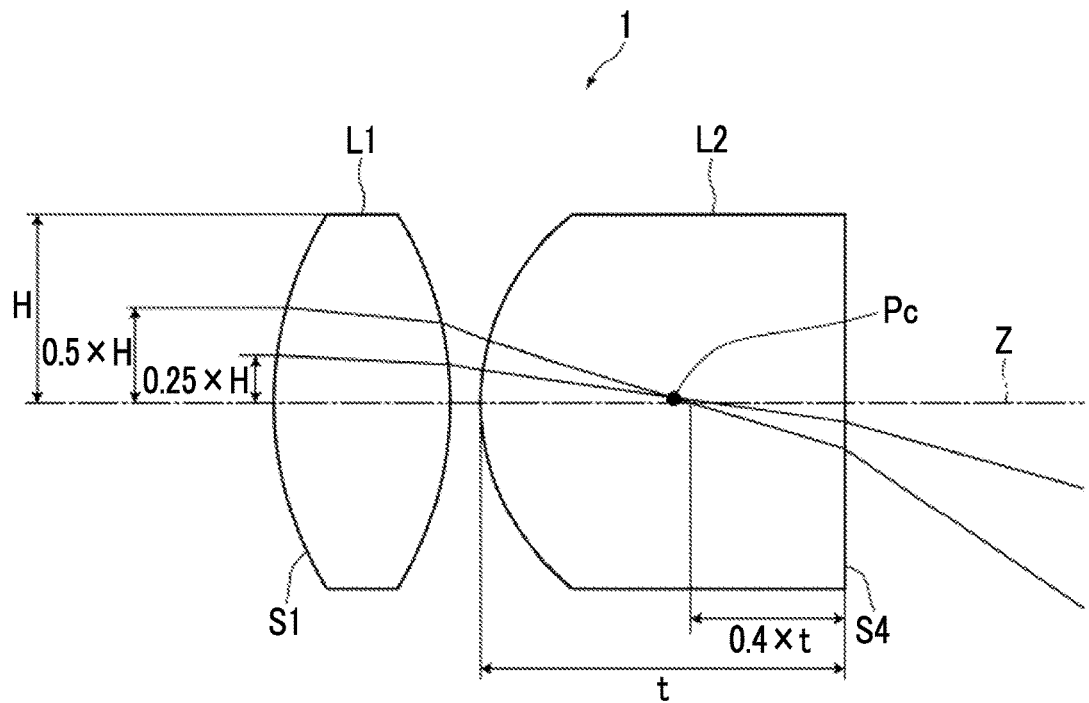
FIG. 1 is a cross-sectional view illustrating the structure of an illumination lens according to an embodiment of the invention.
Figure 2:
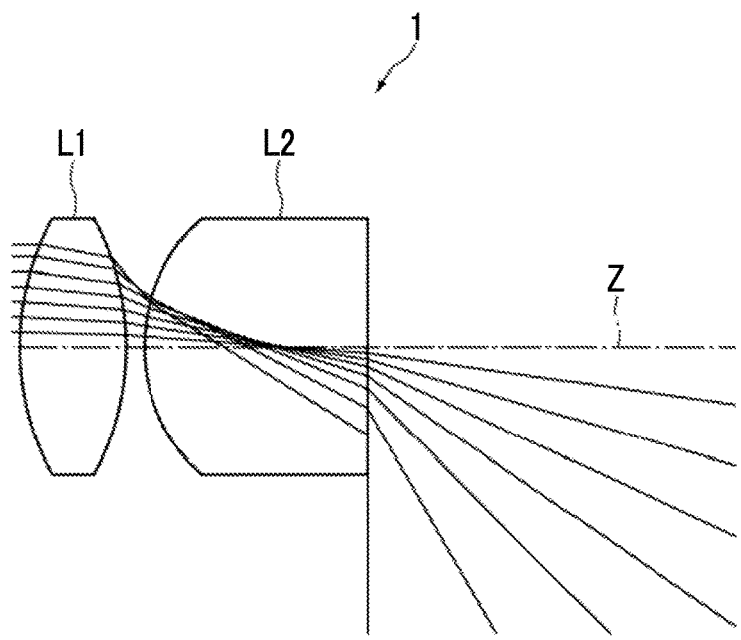
FIG. 2 is a cross-sectional view showing the structure of an illumination lens of Example 1 of the invention and optical paths.

An embodiment of the invention will be described in detail below with reference to the drawings. FIG. 1 is a cross-sectional view showing the structure of an illumination lens 1 according to an embodiment of the invention. FIG. 2 is a diagram showing the structure of the illumination lens 1 and optical paths in a case in which rays are incident on the illumination lens 1 in parallel to an optical axis Z. An example of the structure shown in FIGS. 1 and 2 corresponds to the illumination lens 1 of Example 1 to be described later. The illumination lens 1 is used in an illumination optical system for an endoscope, and light generated from a light source is incident on the illumination lens 1, and the illumination lens 1 emits illumination light to an object to be observed (hereinafter, referred to as an object). FIGS. 1 and 2 are cross-sectional views including the optical axis Z, and a left side in the plane of FIGS. 1 and 2 is shown as a light source side and a right side in the plane of FIGS. 1 and 2 is shown as an object side.

The illumination lens 1 consists of two lenses that are a first lens L1 and a second lens L2 arranged in this order toward the object side from the light source side. In the embodiment shown in FIG. 1, each of the first and second lenses L1 and L2 is a lens having a positive optical power. The illumination lens 1 is composed so that the surfaces of all the lenses have a planar shape or a convexly spherical shape. The surface of the first lens L1 facing the light source side is an incident surface S1 on which light generated from the light source is to be incident, and the incident surface S1 of the first lens L1 is formed to become a convex surface.

The surface of the second lens L2 facing the object side is an emission surface S4 from which light toward the object is to be emitted, and the emission surface S4 of the second lens L2 is formed to become a flat surface. Since the illumination lens 1 is disposed at the distal end of an insertion part of the endoscope in a case in which the illumination lens 1 is to be mounted on an insertable endoscope, there is a concern that the emission surface S4 may be exposed to body fluid, a cleaning solution, oil and fat, and the like. For this reason, in a case in which the emission surface S4 is formed of a flat surface, it is difficult for the liquid, oil and fat, and the like to adhere to the emission surface S4 and the liquid, oil and fat, and the like easily come off even though the liquid, oil and fat, and the like adhere to the emission surface S4. Accordingly, it is easy to clean the emission surface S4.

The illumination lens 1 is composed so that an intersection Pc of a ray incident on the incident surface S1 of the first lens L1 in parallel to the optical axis Z at a height of 0.25×H from the optical axis Z and a ray incident on the incident surface S1 of the first lens L1 in parallel to the optical axis Z at a height of 0.5×H from the optical axis Z is positioned only inside the illumination lens 1 in a case in which the outer diameter of the first lens L1 in a direction perpendicular to the optical axis Z is denoted by 2H. Luminous flux converged inside the illumination lens 1 is emitted to the outside of the illumination lens 1 as divergent light as understood from FIG. 2, and it is said that this light is not likely to invade an object. Since light density is high in a region close to the optical axis Z, high energy is likely to be generated in the region close to the optical axis. However, in a case in which the intersection Pc is positioned only inside the illumination lens 1, it is easy that luminous flux close to the optical axis Z is converged inside the illumination lens 1 once and is then diverged and emitted to the outside of the illumination lens 1. Accordingly, the light density outside the lens can be lowered and light can be changed to low-invasive light. Further, since luminous flux is converged inside the illumination lens 1 once and is then emitted to the outside of the illumination lens 1 as divergent light, a range of a wide angle, for example, 140° or more in the entire angle can be illuminated. Particularly, an angle is effectively given to rays, which are close to the optical axis and of which the quantity of light is likely to be increased.

Further, in a case in which the thickness of the second lens L2 along the optical axis is denoted by t as shown in FIG. 1, the position of the intersection Pc in the direction of the optical axis is positioned closer to the light source than a position, which is apart from the emission surface S4 of the second lens L2 to the light source side by 0.4×t. Accordingly, since it is easy to make the intersection Pc be present inside the illumination lens 1 even though there is a variation caused by manufacturing tolerance, it is possible to improve robustness in changing light to low-invasive light. Further, since diffracted light caused by scratches can be relatively suppressed even though scratches or the like are present on the emission surface S4, the unevenness of illumination light can be reduced.

Furthermore, the illumination lens 1 is formed so as to satisfy the following Conditional Expression (1) in a case in which the focal length of the illumination lens 1 is denoted by f and the focal length of the first lens L1 is denoted by f1. In a case in which f/f1 is set so as not to be equal to or lower than the lower limit of Conditional Expression (1), the light density outside the optical system can be lowered. Accordingly, light can be changed to low-invasive light and a wide emission angle can be ensured. In a case in which f/f1 is set so as not to be equal to or higher than the upper limit of Conditional Expression (1), a force for bending a ray is not excessively increased. Accordingly, even though there is a variation caused by manufacturing tolerance, an influence of the variation is not excessively increased. As a result, it is easy to maintain suitable light distribution and the uniformity of illumination light. In a case in which the illumination lens 1 satisfies the following Conditional Expression (1-1), better characteristics can be obtained.

$$0.61 < f/f1 < 1.5 \tag{1}$$

$$0.62 < f/f1 < 1.49 \tag{1-1}$$

Further, it is preferable that the illumination lens 1 satisfies the following Conditional Expression (2) in a case in which the refractive index of the first lens L1 with respect to a d line is denoted by Nd1. In a case in which Nd1 is set so as not to be equal to or lower than the lower limit of Conditional Expression (2), the light density outside the optical system can be lowered. Accordingly, light can be changed to low-invasive light and a wide emission angle can be ensured. In a case in which Nd1 is set so as not to be equal to or higher than the upper limit of Conditional Expression (2), a suitable material can be selected from existing optical materials so that a change depending on a wavelength can be suppressed even in the case of wide-angle light distribution. Accordingly, the illumination lens is advantageous in obtaining good illumination light. Since the wavelengths of light used in observation methods vary in an endoscope, a change caused by a color, that is, a color shift is required to be less in a certain observation method. In a case in which the illumination lens 1 satisfies the following Conditional Expression (2-1), better characteristics can be obtained.

$$1.8 < Nd1 < 2 \tag{2}$$

$$1.83 < Nd1 < 2 \tag{2-1}$$

Furthermore, it is preferable that the illumination lens 1 satisfies the following Conditional Expression (3) in a case in which the focal length of the illumination lens 1 is denoted by f and the focal length of the second lens L2 is denoted by f2. In a case in which f/f2 is set so as not to be equal to or lower than the lower limit of Conditional Expression (3), a wide emission angle can be ensured. In a case in which f/f2 is set so as not to be equal to or higher than the upper limit of Conditional Expression (3), a force for bending a ray is not excessively increased. Accordingly, even though there is a variation caused by manufacturing tolerance, an influence of the variation is not excessively increased. As a result, it is easy to maintain suitable light distribution and the uniformity of illumination light. In a case in which the illumination lens 1 satisfies the following Conditional Expression (3-1), better characteristics can be obtained.

$$0.4 < f/f2 < 1.8 \tag{3}$$

$$0.45 < f/f2 < 1.75 \tag{3-1}$$

Further, it is preferable that the illumination lens 1 satisfies the following Conditional Expression (4) in a case in which the refractive index of the second lens L2 with respect to a d line is denoted by Nd2. In a case in which Nd2 is set so as not to be equal to or lower than the lower limit of Conditional Expression (4), a wide emission angle can be ensured. In a case in which Nd2 is set so as not to be equal to or higher than the upper limit of Conditional Expression (4), a suitable material can be selected from existing optical materials so that a change depending on a wavelength can be suppressed even in the case of wide-angle light distribution. Accordingly, the illumination lens is advantageous in obtaining good illumination light. In a case in which the illumination lens 1 satisfies the following Conditional Expression (4-1), better characteristics can be obtained.

$$1.8 < Nd2 < 2 \tag{4}$$

$$1.83 < Nd2 < 2 \tag{4-1}$$

Since the above-mentioned preferred structure and/or possible structures can be randomly combined, it is preferable that the above-mentioned preferred structure and/or possible structures are appropriately selectively employed according to specifications to be required. According to this embodiment, it is possible to realize an illumination lens that has high robustness in changing light to low-invasive light.

Next, numerical examples of the illumination lens of the invention will be described.

Example 1

FIG. 2 shows the structure of an illumination lens 1 of Example 1 and optical paths in a case in which rays parallel to the optical axis Z are incident on the lens. A left side in the plane of FIG. 2 is a light source side, and a right side in the plane of FIG. 2 is an object side. The illumination lens 1 consists of a first lens L1 as a biconvex lens and a second lens L2 as a plano-convex lens that are arranged in this order toward the object side from the light source side.

The basic lens data of the illumination lens 1 of Example 1 is shown in Table 1. In Table 1, the surface of a component closest to the light source is written as 1 and the surface number, which is sequentially increased toward the object side, is written in the column of surface number, the radii of curvature of the respective surfaces are written in the column of the radius of curvature, and an interval between each surface and the next surface on the optical axis Z is written in the column of surface spacing. Further, the refractive index of each optical element with respect to a d line (a wavelength of 587.6 nm (nanometer)) is written in the column of Nd, and Abbe's number of each optical element based on the d line is written in the column of vd. Here, the sign of the radius of curvature is positive in a case in which the shape of a surface is convex toward the light source side, and is negative in a case in which the shape of a surface is convex toward the object side. The outer shape 2H of the illumination lens 1 of Example 1 is 1.7.

mm (millimeter) is used as the unit of a length in the data of Table 1, but other appropriate units can also be used since an optical system can be used even though being proportionally increased or reduced in size. Further, numerical values, which are rounded off to a predetermined place, are written in each Table to be described below. Since the symbol, the meaning, and the description method of each data mentioned in the description of Example 1 are the same as those of data in Example 2 to be described later, the repeated description thereof will be omitted below.

TABLE 1

| Example 1 | | | | |
|---|---|---|---|---|
| Surface Number | Radius of Curvature | Surface Spacing | Nd | vd |
| 1 | 1.8180 | 0.7000 | 1.88299 | 40.78 |
| 2 | −1.8180 | 0.1200 | | |
| 3 | 1.1750 | 1.4500 | 1.88299 | 40.78 |
| 4 | ∞ | | | |

Example 2

Figure 3:
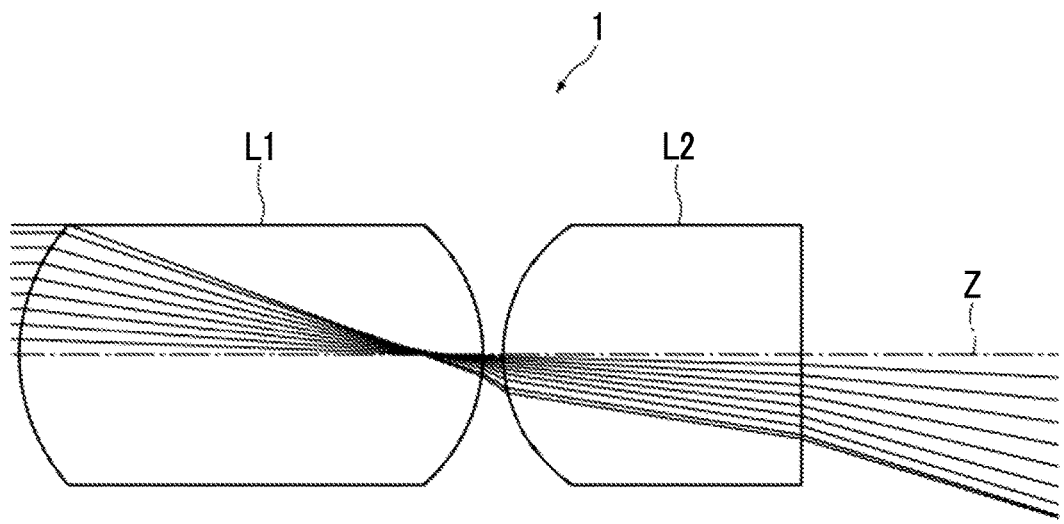
FIG. 3 is a cross-sectional view showing the structure of an illumination lens of Example 2 of the invention and optical paths.

FIG. 3 shows a cross-sectional view showing the structure of an illumination lens 1 of Example 2 and optical paths in a case in which rays parallel to the optical axis Z are incident on the lens. The basic lens data of the illumination lens 1 of Example 2 is shown in Table 2. An outer shape 2H is 1.7 in the illumination lens 1 of Example 2.

TABLE 2

Example 2

| Surface Number | Radius of Curvature | Surface Spacing | Nd | vd |
|---|---|---|---|---|
| 1 | 1.3089 | 2.9654 | 1.90043 | 37.37 |
| 2 | −1.1446 | 0.1287 | | |
| 3 | 1.0433 | 1.9018 | 1.88299 | 40.78 |
| 4 | ∞ | | | |

Table 3 shows corresponding values of Conditional Expressions (1) to (4) with regard to the illumination lenses 1 of Examples 1 and 2. A d line is used as a reference wavelength in Examples 1 and 2, and values shown in Table 3 are values based on the reference wavelength.

TABLE 3

| Expression Number | | Example 1 | Example 2 |
|---|---|---|---|
| (1) | f/f1 | 0.62 | 1.26 |
| (2) | Nd1 | 1.88299 | 1.90043 |
| (3) | f/f2 | 0.53 | 1.69 |
| (4) | Nd2 | 1.88299 | 1.88299 |

Figure 4:
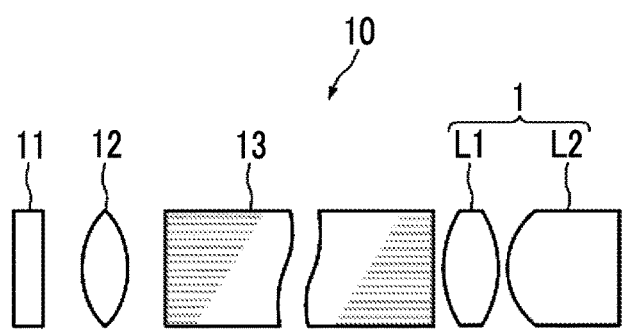
FIG. 4 is a diagram showing the schematic structure of an illumination optical system for an endoscope according to an embodiment of the invention.

Next, an illumination optical system 10 for an endoscope according to an embodiment of the invention will be described. FIG. 4 is a diagram showing the schematic structure of the illumination optical system 10 for an endoscope according to the embodiment of the invention. The illumination optical system 10 for an endoscope includes a light source 11, an optical coupling lens 12, a light guide member 13, and the illumination lens 1 according to the embodiment of the invention. The illumination lens 1 consists of two lenses, that is, a first lens L1 and a second lens L2. For example, a light emitting diode (LED) or a laser can be used as the light source 11. The optical coupling lens 12 is a lens that optically couples the light source 11 to the light guide member 13. The light guide member 13 is to guide light, which is generated from the light source 11, to the illumination lens 1. For example, a light guide formed of a fiber bundle can be used as the light guide member 13. Since the illumination optical system 10 for an endoscope includes the illumination lens 1 according to the embodiment of the invention, the illumination optical system 10 for an endoscope has wide-angle light distribution characteristics and can obtain low-invasive illumination light.

The invention has been described above using embodiments and examples, but is not limited to the embodiments and examples and may have various modifications. For example, the radius of curvature, the surface spacing, the refractive index, and Abbe's number of each lens are not limited to the values mentioned in each numerical example, and may take other values. Further, the illumination lens of the invention can also be applied to an illumination optical system other than the illumination optical system for an endoscope.

What is claimed is:

1. An illumination lens that is used in an illumination optical system for an endoscope, the illumination lens consisting of two lenses consisting of a first lens and a second lens arranged in this order toward an object side from a light source side,
wherein surfaces of all the lenses have a planar shape or a convexly spherical shape,
an incident surface of the first lens on which light generated from a light source is to be incident is a convex surface,
an emission surface of the second lens from which light toward an object is to be emitted is a flat surface,
an intersection of a ray incident on the incident surface in parallel to an optical axis at a height of 0.25×H from the optical axis and a ray incident on the incident surface in parallel to the optical axis at a height of 0.5×H from the optical axis is positioned only inside the illumination lens in a case in which an outer diameter of the first lens in a direction perpendicular to the optical axis is denoted by 2H,
in a case in which a thickness of the second lens along the optical axis is denoted by t, a position of the intersection in a direction of the optical axis is positioned closer to the light source than a position, which is apart from the emission surface of the second lens to the light source side by 0.4×t, and
Conditional Expression (1) expressed by "0.61<f/f1<1.5 . . . (1)" is satisfied in a case in which a focal length of the illumination lens is denoted by f and a focal length of the first lens is denoted by f1.

2. The illumination lens according to claim 1, wherein Conditional Expression (2) expressed by "1.8<Nd1<2 . . . (2)" is satisfied in a case in which a refractive index of the first lens with respect to a d line is denoted by Nd1.

3. The illumination lens according to claim 1, wherein Conditional Expression (3) expressed by "0.4<f/f2<1.8 . . . (3)" is satisfied in a case in which a focal length of the second lens is denoted by f2.

4. The illumination lens according to claim 1, wherein Conditional Expression (4) expressed by "1.8<Nd2<2 . . . (4)" is satisfied in a case in which a refractive index of the second lens with respect to a d line is denoted by Nd2.

5. The illumination lens according to claim 1, wherein Conditional Expression (1-1) expressed by "0.62<f/f1<1.49 . . . (1-1)" is satisfied.

6. The illumination lens according to claim 2, wherein Conditional Expression (2-1) expressed by "1.83<Nd1<2 . . . (2-1)" is satisfied.

7. The illumination lens according to claim 3, wherein Conditional Expression (3-1) expressed by "0.45<f/f2<1.75 . . . (3-1)" is satisfied.

8. The illumination lens according to claim 4, wherein Conditional Expression (4-1) expressed by "1.83<Nd2<2 . . . (4-1)" is satisfied.

9. An illumination optical system for an endoscope comprising:
the illumination lens according to claim 1.

* * * * *